United States Patent [19]

Funk et al.

[11] Patent Number: 5,220,102

[45] Date of Patent: Jun. 15, 1993

[54] PROCESS FOR SEPARATING NORMAL OLEFINS FROM NON-NORMAL OLEFINS

[75] Inventors: Gregory A. Funk, Carol Stream; James R. Lansbarkis, Wood Dale; Anil R. Oroskar, Downers Grove; Beth McCulloch, Clarendon Hills, all of Ill.

[73] Assignee: UOP, Des Plaines, Ill.

[21] Appl. No.: 895,769

[22] Filed: Jun. 9, 1992

Related U.S. Application Data

[63] Continuation-in-part of Ser. No. 811,864, Dec. 23, 1991.

[51] Int. Cl.$^5$ ............................................... C07C 7/13
[52] U.S. Cl. ..................................... 585/829; 585/820; 585/826
[58] Field of Search ................ 585/820, 809, 826, 829

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,146,277 | 8/1964 | Hawes et al. | 585/829 |
| 3,422,848 | 1/1969 | Liebman et al. | 137/625.15 |
| 3,706,812 | 12/1972 | De Rosset et al. | 260/674 SA |
| 4,061,724 | 12/1977 | Grose et al. | 423/355 |
| 4,073,865 | 2/1978 | Flanigen et al. | 423/339 |
| 4,104,294 | 8/1978 | Grose et al. | 260/448 C |
| 4,119,678 | 10/1978 | Neuzil et al. | 208/310 Z |
| 4,290,881 | 9/1981 | Dielacher et al. | 585/826 |
| 4,309,281 | 1/1982 | Dessau | 208/310 |
| 4,455,445 | 6/1984 | Neuzil et al. | 585/820 |
| 4,486,618 | 12/1984 | Kulprathipanja et al. | 585/829 |
| 4,642,397 | 2/1987 | Zinnen et al. | 568/934 |

FOREIGN PATENT DOCUMENTS 0372938 6/1990 European Pat. Off. .
0372939 6/1990 European Pat. Off. .

OTHER PUBLICATIONS

"Silicalite, A New Hydrophobic Crystalline Silica Molecular Sieve;" Nature, vol. 271, Feb. 9, 1978.

D. B. Broughton, "Continuous Adsorptive Processing—A New Separation Technique" presented at the 34th Annual Meeting of the Society of Chemical Engineers at Tokyo, Japan on Apr. 2, 1969.

Primary Examiner—Anthony McFarlane
Attorney, Agent, or Firm—Thomas K. McBride; John F. Spears, Jr.; Jack H. Hall

[57] ABSTRACT

A chromatographic process for separating linear olefins from mixtures with branched-chain olefins with a high silica zeolitic molecular sieve, e.g., silicalites, ZSM-5, etc., having low acid catalytic reactivity, which selectively adsorbs the normal olefins, and uses ketones as desorbents.

7 Claims, 3 Drawing Sheets

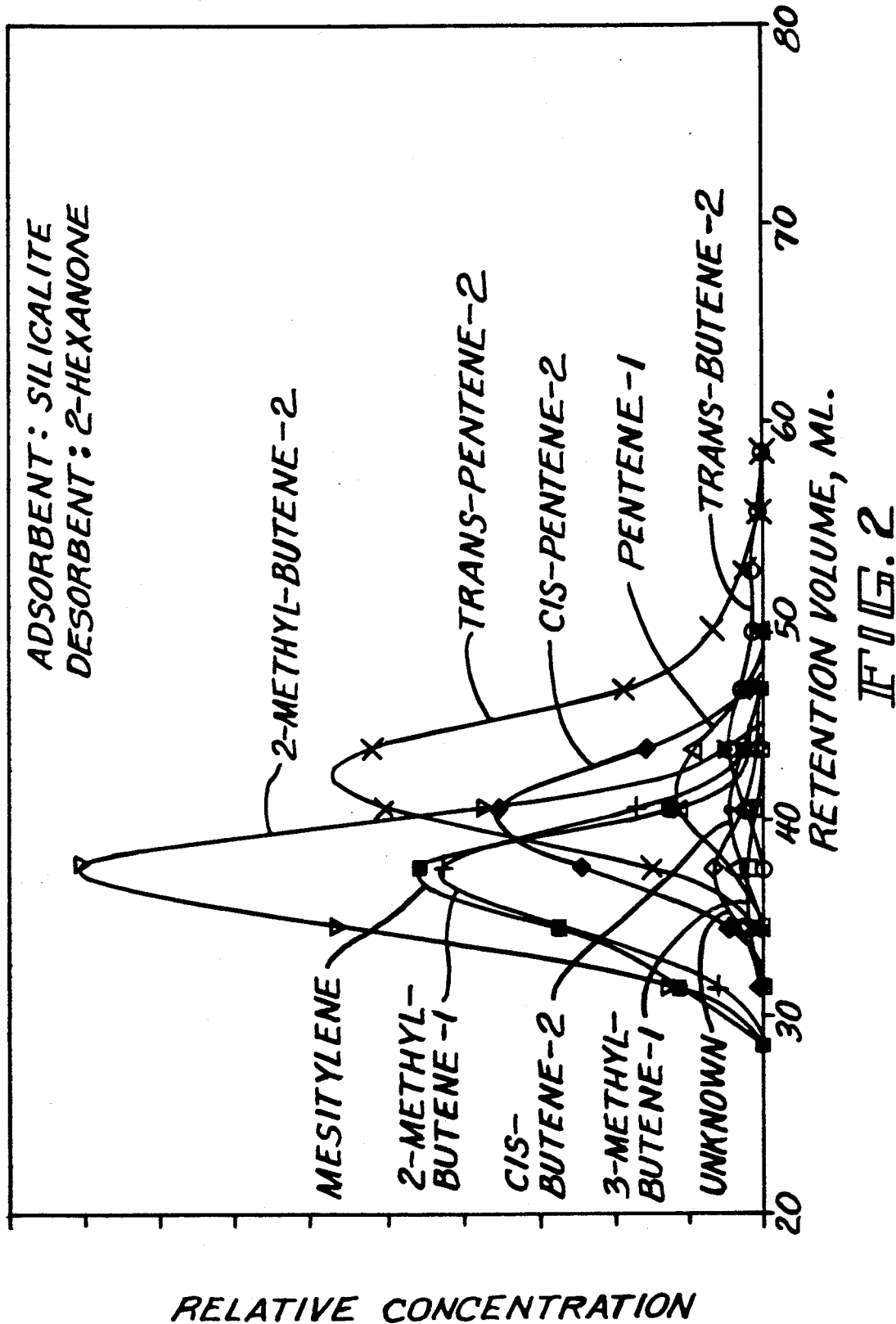

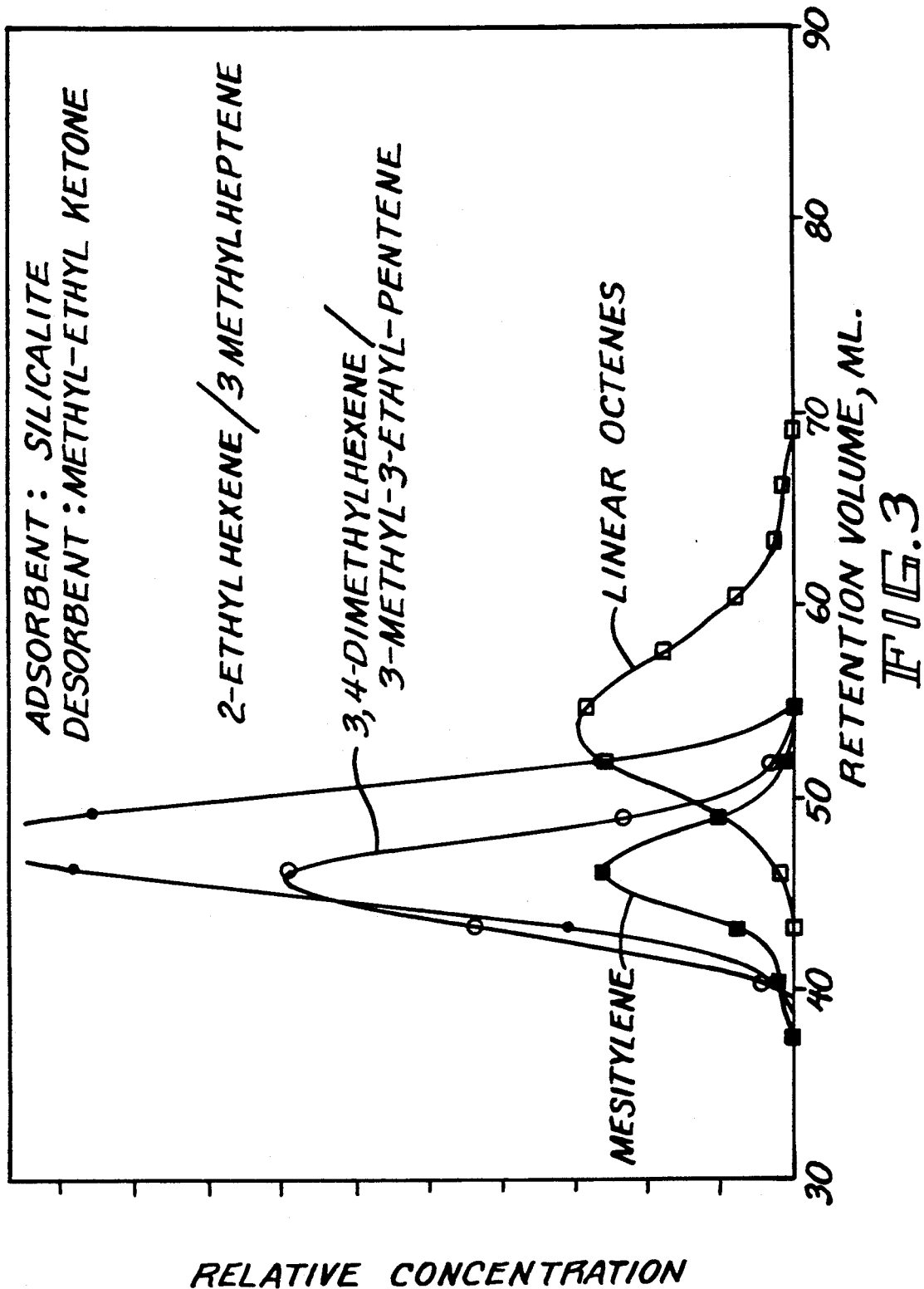

PROCESS FOR SEPARATING NORMAL OLEFINS FROM NON-NORMAL OLEFINS

CROSS REFERENCE TO RELATED APPLICATION

This is a continuation-in-part of patent application U.S. Ser. No. 811,864 filed Dec. 23, 1991, now pending.

FIELD OF THE INVENTION

The field of art to which this invention pertains is the separation of normal $C_5$ to $C_8$ olefins from mixtures thereof with non-normal $C_5$ to $C_8$ olefins.

BACKGROUND OF THE INVENTION

The separation of many classes of compounds by selective adsorption is well known. Also, separations of various mixtures containing olefins into their components are known, e.g., the preferential adsorption of linear olefins over branched olefins using adsorbents such as ZSM-5 and silicalite from Dessau 4,309,281 and Grose et al 4,061,724, the separation of normal $C_4$ olefins from isobutylene with silicalite and pentene-1 as desorbent from Neuzil et al U.S. Pat. No. 4,455,445, and the separation of normal $C_6$ olefins from branched-chain and/or cyclic olefin hydrocarbons with silicalite and pentene-1 or butene-1 as desorbent from Kulprathipanja et al U.S. Pat. No. 4,486,618.

European Patent Applications 0 372 938 and 0 372 939 disclose a method for treating silicalite or ZSM-5 zeolites to enable the treated adsorbents to selectively adsorb n-olefins and n-paraffins from $C_9$–$C_{19}$ hydrocarbon mixtures thereof with branched olefins, branched paraffins, aromatic hydrocarbons and sulfur-containing compounds without catalyzing reactions of the olefinic feed materials. The adsorbent is first treated with an acid and subsequently treated with a base to remove residual acidity, e.g., from the adsorbent itself or from the binder, such as silica, so as to reduce acid catalytic activity.

Neuzil et al U.S. Pat. No. 4,455,445 discloses the separation of normal $C_4$ hydrocarbons from isobutylene with silicalite adsorbent. The adsorbed normal $C_4$ hydrocarbons are desorbed with pentene-1. The patentees also suggest advantages of diluting the desorbent with a material which will not be selectively retained by the molecular sieve (i.e., not capable of acting as a desorbent), e.g., iso-octane.

Kulprathipanja et al U.S. Pat. No. 4,486,618 discloses the separation of normal $C_6$ olefins from $C_6$ branched-chain olefins and $C_6$ cyclic hydrocarbons with crystalline silica molecular sieves and recovering normal $C_6$ olefins by desorption with pentene-1 or butene-1. Iso-octane may be mixed with the desorbent to function as a carrier and diluent.

The invention herein can be practiced in fixed or moving adsorbent bed systems, but the preferred system for this separation is a countercurrent simulated moving bed system, such as described in Broughton et al U.S. Pat. No. 2,985,589 and a paper entitled "Continuous Adsorptive Processing—A New Separation Technique," by D. B. Broughton presented at the 34th Annual Meeting of the Society of Chemical Engineers at Tokyo, Japan on Apr. 2, 1969, both of which are incorporated herein by reference. Cyclic advancement of the input and output streams can be accomplished by a manifolding system or by rotary disc valves, which are also known, e.g., shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

We have discovered that certain desorbents are superior to the n-olefin and n-paraffin desorbents of the prior art in the separation of normal and branched-chain olefinic products and the recovery of the product streams from the adsorbent, silicalite, used to separate the products. With this combination of adsorbent and desorbent, normal olefins are selectively adsorbed relative to branched-chain olefins and cyclic olefins in the feed and the adsorbed normal olefins can be desorbed with less "tailing" than prior art desorbents, e.g., olefins, paraffins, cycloparaffins. This desorbed extract stream is a valuable product which can be used for the production of alcohols. The relatively non-adsorbed branched-chain olefins and cyclic olefins are eluted as raffinate, and are also useful products, e.g., for making synthetic elastomers and as blending agents for gasoline.

SUMMARY OF THE INVENTION

The present invention is a process for separating normal olefins from a mixture of the said normal olefins with branched-chain olefins having 5 to 8 carbon atoms comprising contacting said mixture at adsorption conditions with a molecular sieve comprising crystalline silica having a silica to alumina mole ratio of at least about 300 and preferably greater than 700, removing said relatively non-adsorbed branched-chain olefins from contact with said molecular sieve and recovering said normal olefins by desorption at desorption conditions with a desorbent comprising a ketone having from 3 to 8 carbon atoms. Other embodiments of our invention encompass details about feed mixtures, adsorbents, desorbent materials and operating conditions, all of which are hereinafter disclosed in the following discussion.

BRIEF DESCRIPTION OF THE DRAWINGS

FIG. 2 is the chromatographic plot of the separation of linear pentenes from branched-chain $C_5$ olefins with silicalite and n-hexanone desorbent conducted in Example I.

FIG. 3 is the chromatographic plot of the separation of linear octenes from branched-chain $C_8$ olefins in Example II with silicalite and methylethylketone desorbent.

DETAILED DESCRIPTION OF THE INVENTION

Figure 1:
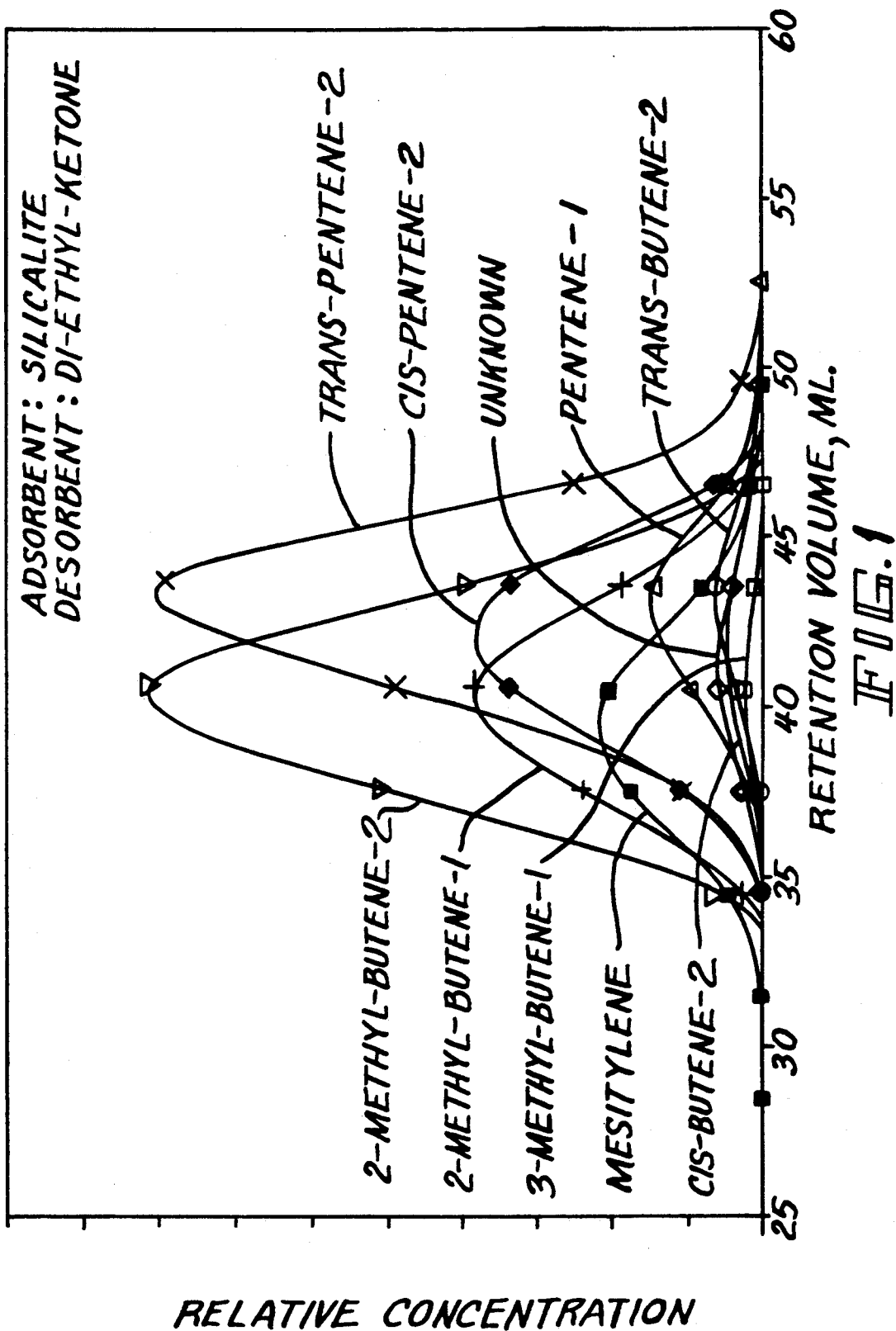
FIG. 1 is the chromatographic plot of the separation of linear pentenes from branched-chain $C_5$ olefins conducted in Example I with silicalite and diethylketone desorbent.

The preferred adsorbents for this separation are the high silica zeolites having a silica:alumina mole ratio of at least about 300, including ZSM-5 and silicalite, and a pore size of about 6 Angstroms in diameter. Such zeolites, and their preparation, are well known, for example, from U.S. Pat. Nos. 4,309,281 to Dessau and 4,061,724 and 4,104,294 to Grose et al. A more detailed discussion of silicalite may be found in the article, "Silicalite, A New Hydrophobic Crystalline Silica Molecular Sieve;" Nature, Vol. 271, Feb. 9, 1978, incorporated herein by reference. Also useful are fluoride silicalites, such as those described in U.S. Pat. No. 4,073,865 to Flanigen et al. The fluoride silicalites have a pore diameter of about 6 Angstroms. Fluoride silicalites are exceptionally inert and do not catalyze olefinic reactions. The silicalites used in the separation process of the invention have silica to alumina ratios ($SiO_2/Al_2O_3$) of at least 300 and preferably in the range of 700 to 1000. The base-treated adsorbents disclosed in EP 0 372 938 and EP 0 372 939, supra, are also reportedly effective in reducing acid catalytic activity and may also be used in the invention. A particularly preferred adsorbent is prepared by loading silica-bonded silicalite with silica to alumina ratios greater than 700 with sodium bicarbonate prior to calcination at 850° C.

The adsorbents are preferably bonded with a binder material, such as silica, which is an amorphous material having channels and cavities enabling access by the components to be separated and by the desorbent to the adsorbent. The binder aids in forming or agglomerating the crystalline particles of the silicalite which otherwise would comprise a fine powder.

The silicalite molecular sieve may then be formed into particles such as extrudates, aggregates, tablets, macrospheres or granules having a desired particle range, preferably from about 16 to about 60 mesh (Standard U.S. Mesh) (1.9 mm to 230 $\mu$m).

Colloidal amorphous silica is an ideal binder for silicalite in that it exhibits essentially no reactivity with olefins in the feed. A silica marketed by DuPont Co. under the trademark Ludox and another marketed by Nalco Chemical Co. (1034) are preferred. The silicalite powder is dispersed in the colloidal amorphous silica which is then gelled and may be further treated in a manner so as to substantially eliminate hydroxyl groups, such as by thermal treatment in the presence of oxygen at a temperature from about 450° C. to about 850° C. for a minimum period from about 3 hours to about 48 hours. The silicalite should be present in the silica matrix in amounts ranging from about 75 wt. % to about 98 wt. % silicalite based on volatile-free composition.

The extruded bonded silicalite particles are thoroughly mixed with a solution of a soluble alkali metal compound, such as sodium bicarbonate, sodium phenoxide, sodium methoxide, sodium hyponitrite, sodium iodate, sodium tartrate, sodium thiosulfate, potassium hypochlorite, potassium carbonate, potassium nitride, potassium oxalate, potassium succinate, rubidium bicarbonate, rubidium dichlorobromide and rubidium sulfate. Finally, the mixture is dried and calcined at a temperature of least 700° C., up to about 1000° C., preferably in the range 800° C. to 900° C. This adsorbent has been determined to be virtually non-reactive under conditions of the adsorption separation of the invention (i.e., no isomerization or formation of heavy products when olefinic feed is contacted with the adsorbent overnight in a pressure vessel, such as a Parr bomb, at 175° C.).

The adsorbent may be employed in the form of a dense fixed bed which is alternately contacted with a feed mixture and a desorbent material in which case the process will be only semicontinuous. In another embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. In a preferred embodiment, therefore, the process will use such flow systems. In a more preferred embodiment, the process will employ a simulated moving-bed countercurrent flow system. The operating principles and sequence of operation of one such simulated moving-bed countercurrent flow system are described in U.S. Pat. No. 2,985,589 incorporated herein by reference.

The separation process of the invention can be practiced using any feed containing a mixture of normal olefins and branched-chain olefins having from 5 to 8 carbon atoms. The olefins may be narrow boiling point fractions, such as $C_5$ to $C_6$, etc., or may have a single carbon number, e.g., pentenes, hexenes, heptenes or octenes. In a preferred process, any paraffins are removed first so that one product of the separation is substantially pure linear olefins and the other product is branched-chain olefins. The paraffins can be removed by an adsorptive separation such as described above using, for example, an X or Y zeolite exchanged with an alkali metal ion, e.g., sodium. The olefins (linear and branched) are desorbed and recovered from the extract stream after removing a raffinate stream containing the paraffins. The paraffin-containing raffinate mixture may be separated into normal and iso-paraffin streams by a similar adsorptive separation process using a Linde 5A zeolite molecular sieve and a liquid paraffinic desorbent having a boiling point different from the feed. The feed to the first stage of the three-stage separation, i.e., for separating olefin from paraffin hydrocarbons, described in this paragraph can be a dimerized $C_5$ cut from a steam-cracked hydrocarbon from which cyclopentadiene has been removed by dimerization and isoprene has been removed by solvent extraction. The extract from the first stage contains normal and branched-chain olefins and becomes the feed for the separation process of the invention.

Other sources of feed mixture which may be separated by the process of the invention are: olefinic streams from catalytic cracking and Fischer-Tropsch reactions.

The general scheme for adsorptive separations is known from the aforesaid U.S. Pat. No. 2,985,589. Briefly, the less absorbed feed component(s) is eluted from the non-selective void volume and weakly adsorbing volume before the more strongly adsorbed component(s). The relatively unadsorbed component(s) is thereby recovered in the raffinate. The relatively adsorbed component(s) is desorbed and recovered in the extract.

The desorbent used in the process for separating normal from non-normal olefins, i.e., straight-chain from branched-chain and cyclic olefins must be strong enough to desorb all of the adsorbed components, in this case, the linear or normal olefins, with reasonable flow rates, without being adsorbed itself so strongly as to prevent the extract component from displacing the desorbent during the following cycle. Thus, in selecting a desorbent, the desorbent preferably is slightly less strongly adsorbed than the extract components. Previously disclosed desorbents for this separation, i.e., olefins, paraffins and cycloparaffins, have been found to be too weak to desorb some of the linear olefins adsorbed by the adsorbent. For example, methylcyclohexane (b.p. 101° C.), in a pulse test with the adsorbent used herein, did not desorb trans-2-butene (a linear olefin contained in the feed) after 116 cc of desorbent flow through the column.

A problem encountered in adsorption separations is the tendency for raffinate components, which are less strongly held by the adsorbent than the extract component(s), to continue to be desorbed by the desorbent with the extract components, thereby reducing the purity of the desired extract product. This tendency is known as "tailing". For some feeds, methylcyclohexane and other prior art desorbents tend to cause the raffinate components to "tail" into the extract, adversely affecting the purity and recovery of the extract product in a commercial plant, and consequently, the economics of the process. Tailing of the extract component(s) into Zone III (desorption zone as described by the Broughton paper, supra) also reduces the recovery of the extract components. The effects of tailing can be reduced by increasing the desorbent flow. However, the increased desorbent flow will increase the equipment and utility costs of the process. Therefore, a stronger desorbent, vis-a-vis the extract products was desired. With the desorbents of the invention, "tailing" can be reduced to lower levels, thereby improving the economics of the separation.

To demonstrate the greater strength of the desorbents of the invention, we compared the ketones preferred herein to the prior art paraffins, olefins and cycloparaffins in pulse tests for separating isopentenes from normal pentenes. In these separations with ketone desorbents, the range of the net retention volume (NRV) (defined hereinafter) of the linear olefins was below that with the other groups of desorbents as set forth in Table 1 below. Also, as a group, the ketones of the invention exhibited increased mass transfer rates as indicated by the lower ranges of peak width at half height (WHH) (defined hereinafter) shown in Table 1.

TABLE 1

| Desorbent | Carbon Range of Desorbent | NRV Range (cc) | WHH Range (cc) |
|---|---|---|---|
| Ketones | 4-7 | 2.2-16.4 | 5.1-15.8 |
| Paraffins | 7-8 | 10.3-32.2 | 8.7-35.5 |
| Octene-1 | 8 | 9.5-29.0 | 6.4-40.2 |
| Methylcyclohexane | 7 | 14.7-23.8 | 10.5-21.7 |

In addition to the selectivity (for the components to be separated and rejected) and mass transfer rates necessary to achieve a good separation, the physical qualities of the desorbent must be matched to the feed stream so that the desorbent may be separated from the product streams by simple fractionation. To take the example of a $C_5$ olefin (pentene) feedstock, where the boiling points of the common isomers present are in the range from about 25° C. to about 36° C., the desorbent is selected to have at least a 5°-10° C. difference from all the feed components. For this separation, ketones from $C_3$ to $C_7$ have acceptable boiling point differences for easy recovery and also good selectivity. The ketones include acetone, methylethylketone, pentanone isomers, hexanone isomers and heptanone isomers. Heptanone-2, however, at temperatures up to at least about 120° C., exhibits tailing to about 100 ml desorbent in the pulse test, which is considered excessive, and is believed to be too weak a desorbent to be commercially viable for the separation of linear pentenes. Hexanone-2, on the other hand, appears superior in selectivity and mass transfer rate for linear $C_5$ olefin separation. At 160° C., the peak widths at half height are low, in the range 6.7 to 7.4 ml. Diethylketone and methylethylketone also have boiling points sufficiently higher than the feed for easy fractionation, good selectivity and slightly shorter peak widths, indicating good mass transfer.

In the separation of $C_8$ olefins, acetone is slightly weak and exhibits some tailing. Methylethylketone is an excellent desorbent and exhibits virtually no tailing at 150° C. The boiling points of $C_5$ and $C_6$ ketones fall too close to those of the octenes and are not easily recovered for fractionation. $C_7$ and $C_8$ (heptanone isomers and octanone isomers) ketones (b.p. 144-150) are suitable heavy desorbents, having sufficient strength to desorb all extract components although selectivities may be lowered.

Although the ketones of the invention might be expected to be reactive in the presence of catalytic sites on the zeolite, it was discovered unexpectedly that whatever short term effects on the adsorbent existed, they were short-lived, without adverse effects on either selectivity or capacity or contamination of product by reaction products. Without being bound by our theory, we believe the acidic reactive sites of the adsorbent were blocked and neutralized by ketone molecules or the products formed by the ketones during the initial reaction period of the adsorbent which were not desorbed, but which did not appear to substantially reduce adsorbent capacity.

Further, it has been found that tailing is dependent to some extent upon the temperature of the separation and that "tailing" can be reduced by maintaining higher temperatures, e.g., above about 100° C. and preferably from 120° to about 200° C.

The preferred desorbents for use in the process for separating normal olefins from non-normal olefins, i.e., branched-chain and cyclic olefins, are ketones having from 3 to 8 carbon atoms and boiling points at least 5° C. higher or lower than the feed material so that the desorbent can be easily recovered for reuse. The preferred desorbent for separating $C_4$ and $C_5$ linear olefins, or mixtures thereof, according to the invention are methylethylketone, diethylketone and 2-hexanone. For separating $C_8$ linear olefins, methylethylketone is the preferred desorbent. These desorbents, in combination with high silica zeolitic adsorbents, are sufficiently strong to substantially lower the "tailing" observed with prior desorbents used in the process and recover all the linear olefins contained in the feed.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor phase operation. Adsorption conditions will include a temperature range of from about 100° C. to about 200° C. and a pressure sufficient to maintain liquid-phase, ranging from about atmospheric to about 400 psig, with from about atmospheric to about 200 psig usually being adequate. Desorption conditions will include the same range of temperatures and pressures as used for adsorption conditions. The preferred temperatures for adsorption and desorption conditions are above about 120° C. and up to about 200° C., since it has been found that tailing can be significantly reduced by operating at temperatures of 120° C. or greater. The most preferred temperature range is 160° C. to 200° C.

At least a portion of the raffinate stream, which contains the concentrated branched-chain olefin product, and at least a portion of the extract stream, which contains the normal olefin product, from the separation process are passed to separation means, typically fractionators or evaporators, where at least a portion of desorbent material is separated to produce a raffinate product and an extract product, respectively. The desorbent material is normally recycled to the adsorption column where it is combined with fresh desorbent.

A dynamic testing apparatus is employed to test various adsorbents with a particular feed mixture and desorbent material to measure the adsorption characteristics of retention, capacity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer such as mesitylene is injected for a duration of several minutes. Desorbent material flow is resumed, and the tracer or the raffinate component (or both) and the extract component are eluted as in a liquid-solid chromatographic operation. The effluent can be analyzed on-stream, or, alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component, i.e., mass transfer rates, with the desorbent material can generally be characterized by the width of the peak envelopes at half intensity, with lower widths, expressed as cubic centimeters of desorbent material, indicating higher rates. Selectivity, $\beta$, is determined by the ratio of the net retention volumes of the more strongly adsorbed component to each of the other components.

The examples shown below are intended to further illustrate the process of this invention without unduly limiting the scope and spirit of said process.

EXAMPLE I

A pulse test as described above was performed to evaluate the process of the present invention for separating a mixture of normal and branched-chain $C_5$ olefins. The column was filled with 70 cc of a modified (sodium silicate) silicalite adsorbent, prepared by an after treatment which eliminates catalytic activity of the adsorbent for olefins. The precursor was silicalite (S-115 available from UOP) with a silica binder (Nalco 1034a). The after treatment consisted of mixing ⅛-inch silicalite extrudate with a 0.5% (wt.) solution of sodium bicarbonate and drying at 550° C. for 1 hour and calcining at 840° C. for 1 hour.

The separation column was maintained at a temperature of 100° C. and a pressure sufficient to provide liquid-phase operations. The sample was 2 cc of a mixture which contained 10% (wt.) mesitylene (tracer) and 90% (wt.) of feed having the approximate composition shown in Table 2 below. The desorbent was diethylketone (pentanone-3). The desorbent material was run continuously at a nominal liquid hourly space velocity (LHSV) of 1.3 (1.50 ml per minute flow rate). At some convenient time interval, the desorbent was stopped and the feed mixture was run for a 1.3 minute interval at a rate of 1.5 ml/min. The desorbent stream was then resumed at 1.3 LHSV and continued to pass into the adsorbent column until all of the feed components had been eluted from the column as determined by analyzing the effluent stream leaving the adsorbent column.

The results of the analyses obtained are shown in FIG. 1. The branched-chain olefins are removed as raffinate near the void volume and the normal olefins are desorbed thereafter. A small amount of n-pentane impurity in the feed was found in the extract. The results are also set forth in the following Table 2 of gross retention volumes (GRV), net retention volumes (NRV) and selectivities ($\beta$).

TABLE 2

| Component | Wt. % in Feed | GRV (ml.) | NRV (ml.) | $\beta$ |
| --- | --- | --- | --- | --- |
| Mesitylene | 10.0 | 39.4 | 0.0 | ∞ |
| 2-Methyl-Butene-2 | 27.4 | 40.1 | 0.7 | 4.57 |
| 2-Methyl-Butene-1 | 13.4 | 40.1 | 0.7 | 4.42 |
| 3-Methyl-Butene-1 | 1.0 | 40.5 | 1.1 | 2.94 |
| Unknown | 1.9 | 41.2 | 1.8 | 1.83 |
| Cis-Pentene-2 | 12.5 | 41.8 | 2.4 | 1.35 |
| Cis-Butene-2 | 2.2 | 42.0 | 2.6 | 1.25 |
| Pentene-1 | 4.6 | 42.7 | 3.3 | 1.00 |
| Trans-Pentene-2 | 24.3 | 42.7 | 3.3 | 0.98 |
| Trans-Butene-2 | 2.7 | 43.0 | 3.6 | 0.90 |

All of the linear olefins, cis- and trans-pentene-2, cis- and trans-butene-2 and pentene-1, were desorbed after all the branched-chain olefins, making a separation possible.

Two additional samples of the same feed were separated in a further pulse tests using the same procedure as above at a temperature of 160° C. The desorbents in pulse tests 2 and 3 were methylethylketone and 2-hexanone, respectively. Similar results were obtained as set forth in the following Table 3 using methylethylketone desorbent. FIG. 2 and Table 4 show the results of the separation using 2-hexanone as desorbent.

TABLE 3

| Component | Wt. % in Feed | GRV (ml.) | NRV (ml.) | β |
| --- | --- | --- | --- | --- |
| Mesitylene | 10.0 | 35.7 | 0.00 | ∞ |
| 2-Methyl-Butene-2 | 27.4 | 36.7 | 1.0 | 4.38 |
| 3-Methyl-Butene-1 | 13.4 | 36.8 | 1.1 | 4.11 |
| 2-Methyl-Butene-1 | 1.0 | 36.8 | 1.1 | 4.07 |
| Unknown | 1.9 | 38.5 | 2.8 | 1.57 |
| Cis-Pentene-2 | 12.5 | 39.0 | 3.3 | 1.34 |
| Cis-Butene-2 | 2.2 | 39.3 | 3.6 | 1.24 |
| Pentene-1 | 4.6 | 40.1 | 4.5 | 1.00 |
| Trans-Pentene-2 | 24.3 | 40.5 | 4.8 | 0.92 |
| Trans-Butene-2 | 2.7 | 41.3 | 5.6 | 0.79 |

TABLE 4

| Component | Wt. % in Feed | GRV (ml.) | NRV (ml.) | β |
| --- | --- | --- | --- | --- |
| Mesitylene | 10.0 | 36.6 | 0.0 | ∞ |
| 2-Methyl-Butene-1 | 27.4 | 36.9 | 0.3 | 18.07 |
| 2-Methyl-Butene-2 | 13.4 | 36.9 | 0.3 | 17.06 |
| 3-Methyl-Butene-1 | 1.0 | 37.0 | 0.4 | 12.20 |
| Unknown | 1.9 | 37.3 | 0.7 | 6.82 |
| Cis-Pentene-2 | 12.5 | 39.8 | 3.3 | 1.55 |
| Cis-Butene-2 | 2.2 | 40.5 | 4.0 | 1.28 |
| Pentene-1 | 4.6 | 41.6 | 5.0 | 1.00 |
| Trans-Pentene-2 | 24.3 | 42.1 | 5.5 | 0.91 |
| Trans-Butene-2 | 2.7 | 44.4 | 7.8 | 0.65 |

EXAMPLE II

A $C_8$ olefin feed having the composition in Table 5 was separated in the same manner as in Example I at 150° C. using the same adsorbent as in Example I. The desorbent was methylethylketone. The results are set forth in FIG. 3 and the following Table 5. Because of the difficulty in analyzing individual components in the complex feed mixture on-line, the eluents from the pulse test were hydrogenated and then analyzed by gas chromatography (GC) for the following groups as paraffins: dialkyl $C_8$ olefins (3,4-dimethylhexane, 3-methyl-3-ethylpentane); alkyl $C_8$ olefins (2-ethylhexane, 3-methylheptane); linear $C_8$ olefins (n-octane).

TABLE 5

| Component | Wt. % in Feed | GRV (ml.) | NRV (ml.) | β |
| --- | --- | --- | --- | --- |
| 3,4-Dimethylhexane/ 3-methyl-3-ethylpentane (dialkyl octenes) | 29.0 | 45.4 | −0.8 | −9.36 |
| Mesitylene | 10.0 | 46.2 | 0.0 | ∞ |
| 2-Ethylhexane/ 3-Methylheptene (alkyl octenes) | 45.5 | 47.4 | 1.2 | 6.56 |
| n-Octane: (linear octenes) | 15.5 | 54.2 | 7.9 | 1.00 |

What is claimed:

1. A process for separating normal olefins from a mixture of the said normal olefins and branched-chain olefins having 5 to 8 carbon atoms comprising contacting said mixture at adsorption conditions with a molecular sieve having low acid catalytic reactivity comprising crystalline silica having a silica to alumina mole ratio of at least about 300 to selectively adsorb said normal olefins, removing said relatively non-adsorbed branched-chain olefins from contact with said molecular sieve and recovering said normal olefins by desorption at desorption conditions with a desorbent comprising a ketone having from 3 to 8 carbon atoms.

2. The process of claim 1 wherein said desorbent is selected from the group consisting of acetone, methylethylketone, pentanone isomers, hexanone isomers, heptanone isomers and octanone isomers.

3. The process of claim 1 wherein said normal olefins and branched-chain olefins are $C_4$ or $C_5$ olefins or mixtures thereof and said desorbent is selected from the group consisting of methylethylketone, diethylketone and 2-hexanone.

4. The process of claim 1 wherein said normal olefins and branched chain olefins are $C_8$ olefins and said desorbent is methylethylketone.

5. The process of claim 1 wherein said adsorbent is a fluoride silicalite.

6. The process of claim 1 wherein said adsorbent is silicalite or ZSM-5.

7. The process of claim 1 wherein said adsorbent has been treated to reduce acid catalytic activity.

* * * * *